(12) United States Patent
Frazier et al.

(10) Patent No.: US 6,627,433 B2
(45) Date of Patent: Sep. 30, 2003

(54) MULTI-CHANNEL ANALYTE-SEPARATION DEVICE EMPLOYING SIDE-ENTRY EXCITATION

(75) Inventors: Jeffery D. Frazier, Redwood City, CA (US); Paul D. Grossman, Hillsborough, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 09/938,767

(22) Filed: Aug. 24, 2001

(65) Prior Publication Data

US 2003/0040010 A1 Feb. 27, 2003

(51) Int. Cl.$^7$ .................. C12M 1/34; G01N 277/447
(52) U.S. Cl. .................. 435/288.7; 435/287.1; 435/288.2; 435/288.4; 436/165; 204/450
(58) Field of Search .................. 436/164, 165, 436/172; 435/287.1, 288.2, 288.7; 422/50, 55, 82.05, 82.06; 204/193, 450, 600, 601

(56) References Cited

U.S. PATENT DOCUMENTS

| | | |
|---|---|---|
| 4,832,815 A | 5/1989 | Kambara et al. |
| 5,114,551 A | 5/1992 | Hjerten et al. |
| 5,192,412 A | 3/1993 | Kambara et al. |
| 5,268,080 A | 12/1993 | Kambara et al. |
| 5,277,780 A | 1/1994 | Kambara |
| 5,314,602 A | 5/1994 | Kambara et al. |
| 5,439,578 A | 8/1995 | Dovichi et al. |
| 5,529,679 A | 6/1996 | Takahashi et al. |
| 5,582,705 A | 12/1996 | Yeung et al. |
| 5,695,626 A * | 12/1997 | Yeung et al. ............ 204/466 |
| 5,741,411 A | 4/1998 | Yeung et al. |
| 5,790,727 A | 8/1998 | Dhadwal et al. |
| 5,833,827 A | 11/1998 | Anazawa et al. |
| 5,867,266 A | 2/1999 | Craighead |
| 6,017,434 A | 1/2000 | Simpson et al. |
| 6,159,353 A | 12/2000 | West et al. |
| 6,236,945 B1 | 5/2001 | Simpson et al. |
| 6,246,046 B1 * | 6/2001 | Landers et al. ............ 204/451 |

FOREIGN PATENT DOCUMENTS

EP 0 840 115 A2 5/1998

OTHER PUBLICATIONS

Huang et al., Acousto–Optical Deflection–Based Laser Beam Scanning for Fluorescence Detection on Multichannel Electrophoretic Microchips, 1999, Anal. Chem., 71(23):5309–5314.*

Wang et al., Microfabricated Electrophoresis Chips for Simultaneous Bioassays of Glucose, Uric Acid, Ascorbic Acid, and Acetaminophen, 2000, Anal. Chem., 72(11):2514–2518.*

Chen et al., Development of a Multichannel Microfluidic Analysis System Employing Affinity Capillary Electrophoresis for Immunoassay, 2001, Anal. Chem., 73(7):1472–1479.*

Tian et al., Capillary and Microchip Electorphoresis for Rapid Detection of known Mutations by Combining Alle–specific DNA Amplification with Heteroduplex Analysis, 2001, Clinical Chem., 42(2):173–185.*

* cited by examiner

Primary Examiner—Andrew Wang
Assistant Examiner—My Chau T Tran
(74) Attorney, Agent, or Firm—Jeffery D. Frazier; Kilyk & Bowersox, P.L.L.C.

(57) ABSTRACT

A side-entry excitation arrangement is provided with a multi-channel analyte-separation device. In various embodiments, a plurality of channels are disposed in an array, with a laser disposed to direct an excitation beam of light along a beam path that crosses the longitudinal axes of the channels, so as to simultaneously irradiate a region of each of the channels. Devices of the invention can be useful, for example, in the separation and analysis of bio-molecules, such as DNA, RNA, etc.

14 Claims, 4 Drawing Sheets

MULTI-CHANNEL ANALYTE-SEPARATION DEVICE EMPLOYING SIDE-ENTRY EXCITATION

FIELD OF THE INVENTION

The present invention relates to electrophoretic separation systems for the analysis of bio-molecules, such as nucleic acids. More particularly, this invention relates to a multi-channel analyte-separation device employing side-entry illumination.

REFERENCES

Backhouse et al., DNA sequencing in a monolithic microchannel device, Electrophoresis 2000, 21, 150–156.
Dolnik et al., Capillary electrophoresis on microchip, Electrophoresis 2000, 21, 41–54.
Grossman and Colburn, Capillary Electrophoresis Theory and Practice, Chapter 1, Academic Press (1992).
Kambara et al., U.S. Pat. No. 5,192,142 (1993).
Madabhushi et al., U.S. Pat. No. 5,552,028 (1996).
Sambrook et al., eds., Molecular Cloning: A Laboratory Manual, Second Edition, Chapter 5, Cold Spring Harbor Laboratory Press (1989).
Woolley et al., Ultra-high-speed DNA fragment separations using microfabricated capillary array electrophoresis chips, Proc. Natl. Acad. Sci., vol. 91, pp. 11348–11352, November 1994, Biophysics.
Yeung et al., U.S. Pat. Nos. 5,741,411 and 5,582,705.

BACKGROUND OF THE INVENTION

Devices for carrying out separations of analytes, such as biomolecules (e.g., proteins, DNA, RNA, etc.), have gained widespread use in recent years.

In electrophoretic separations, it is often desirable to illuminate a plurality of migrating analytes, tagged with excitable reporters (e.g., fluorescent dyes), to stimulate detectable emission indicative of the nature (e.g., identity or composition) of the tagged analytes.

SUMMARY OF THE INVENTION

Various aspects of the present invention provide a multi-channel analyte-separation device (channel device) comprising a substrate defining an array of channels. According to various embodiments, adjacent channels of the device are separated by wall structure, which includes at least a portion that is substantially transparent. The transparent portions are disposed along a path or line crossing (e.g., co-planar and normal to) the longitudinal axes of the channels. An excitation-beam source (e.g., a laser) is adapted to direct an excitation beam of light along the path, such that the beam can simultaneously pass through each of the transparent portions and each of the channels. Plural samples migrating along the various channels, e.g., by electrophoresis, can thus be simultaneously irradiated and detected.

Various embodiments are particularly adapted to biomolecule (e.g., DNA, RNA, PNA, etc.) sequence or other analysis methods, in which each of a plurality of different fragment types is labeled with a spectrally distinctive fluorescent dye. According to certain embodiments, a side-entry laser arrangement at a detection zone of a multi-channel electrophoresis device excites the dyes, while in the channels, to emit light. In various embodiments, emitted light from samples in the channels passes through a laser light filter, through a collection lens, through a transmission dispersion element, which spectrally separates the light, and through a focusing lens. The focused light can be incident on a detector array (e.g., CCD) capable of detecting the simultaneously spatially focused and spectrally diverged light from the detection regions of all the channels. Electronic signals from the detector array can provide information about the character or sequence of the DNA sample.

BRIEF DESCRIPTION OF THE DRAWINGS

The structure and manner of operation of the invention may further be understood by reference to the following description taken in conjunction with the accompanying drawings, in which identical reference numerals identify identical or similar elements, and in which.

DESCRIPTION OF THE INVENTION

Reference will now be made to various embodiments of the invention, examples of which are illustrated in the accompanying drawings. While the invention will be described in conjunction with various preferred embodiments, it will be understood that they are not intended to limit the invention. On the contrary, the invention is intended to cover alternatives, modifications, and equivalents, which may be included within the invention as defined by the appended claims.

Unless stated otherwise, the following terms and phrases as used herein are intended to have the following meanings:

The term "channel" as used herein refers to an elongate, narrow passage or other structure (e.g., grooves, etc.) formed in a substrate and capable of supporting a volume of separation medium and/or buffer solution; e.g., such as is used in carrying out electrophoresis. The geometry of a channel may vary widely. For example, a channel can have a circular, oval, semi-circular, semi-oval, triangular, rectangular, square, or other cross-section, or a combination thereof. Channels can be fabricated by a wide range of technologies, including microfabrication techniques. As used herein, the term "channel" is not intended to encompass a capillary tube.

The terms "capillary" and "capillary tube" as used herein, refer to an elongated tubular or cylindrical structure defining an inner lumen. For example, a capillary can be an elongated capillary or micro-capillary tube made, for example, from fused silica, quartz, silicate-based glass, such as borosilicate glass, phosphate glass, alumina-containing glass, and the like, or other silica-like material(s). As used herein, "capillary" does not encompass a channel in a substrate such as a plate, slide, chip, wafer, or the like.

The term "channel device" refers to a substrate, such as a plate, slide, chip, wafer, or similar structure, including one or more channels (e.g., grooves); and particularly those adapted at least in part for carrying out electrophoresis. Channel devices can take the form, for example, of microfabricated devices (e.g., a grooved, etched, or fluted plate, slide, chip, wafer, or other substrate).

As used herein, the term "sample zone" or "analyte zone" refers to a collection of molecules comprising a subset of sample or analyte components having similar electrophoretic migration velocities such that the molecules of a sample zone or analyte zone migrate as a defined zone. In the limit, such a zone is made up of molecules having identical electrophoretic migration velocities. Sample zones and analyte zones are often referred to as "bands."

As used herein, the term "separation medium" or "separation matrix" refers to a medium in which an electrophoretic separation of sample components can take place. Separation media typically comprise several components, at least one of which is a charge-carrying component, or electrolyte. The charge-carrying component is usually part of a buffer system for maintaining the separation medium at a defined pH. Media for separating polynucleotides, proteins, or other biomolecules having different sizes but identical charge-frictional drag ratios in free solution, further include a sieving component. Such sieving component is typically composed of a cross-linked polymer gel, e.g., cross-linked polyacrylamide or agarose (Sambrook), or a polymer solution, e.g., a solution of polyacrylamide, hydroxyethyl cellulose, and the like (Grossman; Madabhushi).

Various aspects of the present invention provide channel devices useful, for example, in electrophoretic separations of bio-molecules. According to various embodiments, the channel devices employ side-entry excitation geometry. Channel devices herein are to be contrasted with capillary arrangements that employ multiple capillaries (i.e., elongated tubular structures). Rather, the channel devices herein are comprised of a substrate, such as a plate, slide, chip, wafer, or similar structure, including one or more channels (e.g., grooves). The substrate can be a monolithic structure or a multi-layer structure, according to one or more embodiments. In various embodiments, channel devices take the form, for example, of microfabricated devices (e.g., grooved, etched, or fluted plate, slide, chip, wafer, or other substrate). It has previously been suggested by others that channel-device technology was not developed enough to employ side-entry illumination (see Yeung et al., U.S. Pat. No. 5,741,411, col. 8, lines 14–24, and U.S. Pat. No. 5,582,705, col. 8, lines 9–19). To the contrary, the present invention prefers the use of channel devices over multiple capillary (tube) arrangements.

In various embodiments, separation channels are formed on a glass or plastic substrate, such as a plate, slide, wafer, chip, or the like, by microfabrication techniques known in the art, e.g., photolithographical and/or wet-chemical etching procedures, laser ablation, electroforming, microcontact printing, microstamping, micromolding, microcasting, micromachining, engraving, and/or embossing techniques, to name a few. For example, Backhouse et al., Dolnik et al., and Woolley et al (each of which is incorporated herein by reference) discuss certain fabrication techniques that the skilled artisan can employ in making the devices of the present invention. In one embodiment, the separation channels are formed in a generally planar substrate comprised at least in part, for example, of an electrically insulating material, e.g., fused silica, quartz, silicate-based glass, such as borosilicate glass, phosphate glass, alumina-containing glass, and the like, or other silica-like material(s).

Various embodiments of the devices herein are particularly well suited, for example, to fluorescence detection of a fluorescent target species in a sample. According to various embodiments, channels of a channel device are arranged in a coplanar channel array. In various embodiments, the channel array includes at least about 4 (e.g., 8, 12, 16, 24, 48, 96, or more) coplanar, adjacently arranged channels. Sidewall regions of each channel include one or more transparent portions. According to certain embodiments, a transparent portion is transparent to light having a wavelength about equal to a wavelength of a beam of coherent light used to irradiate a target species in a channel. A "transparent portion" or "transparent medium" is one that transmits light with little or no attendant light scattering. For example, a transparent portion can be comprised of an optically clear glass or plastic. According to certain embodiments, the transparent portion is transparent to light having a wavelength of about 200–1500 nm; e.g., about 250–800 nm.

Together, the transparent portions define a transparent path extending through the channel array, e.g., from each channel to the next. In an embodiment, the transparent path comprises a plane extending through the channels, as is the case where the channels are fabricated entirely out of transparent material.

In certain embodiments, the transparent portions of the sidewalls exhibit little or no fluorescence when exposed to a beam of coherent light, so as to reduce or eliminate background fluorescence from the detected fluorescence. For example, the transparent portions can be selected and designed to exhibit substantially no fluorescence when exposed light having a wavelength of 200–1500 nm; e.g., about 250–800 nm. By "substantially no fluorescence" is meant that the level of fluorescence emitted by a transparent portion, if any, is less than observed background fluorescence.

According to various embodiments, detection of a target species can be effected through a transparent portion provided in an upper wall or ceiling region of a channel. Such additional transparent portion can be selected and designed to exhibit substantially no fluorescence when exposed to light having a wavelength about equal to the wavelength of light emitted by a fluorescing target species. In an embodiment, the entire channel device is constructed from a transparent, non-fluorescing material, such as fused silica. Transparent windows may alternatively be formed at or along selected regions of channels.

Instead of, or in addition to, utilizing such transparent portions, one or more sidewalls can include a translucent portion defining a translucent path extending through the array perpendicular to the channels. A translucent medium produces some light scattering when transmitting light. In certain embodiments, transparency is preferred over translucency because of greater light throughput and reduced detection S/N.

As indicated above, side-entry irradiation of target species in multiple channels can be effected through a transparent portion of a sidewall of each channel in a multi-channel array. According to various embodiments, light passes through the transparent portions in the array in a sequential manner. A coherent light source can be positioned to direct a beam of coherent light along the transparent path. A coherent light source produces light waves traveling together in phase. The light can have, for example, a wavelength of about 200–1,500 nm. For example, the coherent light source used can be a laser. An argon ion laser operating simultaneously at one or more visible lines can be used for excitation, although other light sources and wavelengths can be used. Exemplary excitation wavelengths are 488 nm and 514 nm. A pure output laser, i.e., a laser emitting light of a single wavelength, can be a useful light source. Alternatively, the wavelength of the laser can be chosen by an interference filter or a glass prism.

According to various embodiments, the beam of coherent light is focused and collimated through a collimating focusing lens interposed between the coherent light source and the channel array. For example, the collimated excitation beam can have a diameter of less than about 300 micrometers (e.g., less than about 75 or 50 micrometers) while traversing the channels in the array. In an embodiment, including an array comprising about 96 channels, the array width is less than about 1.5 cm, and a lens with a focal length of about 5–30 cm, e.g., about 10 cm, is used to focus and collimate the beam such that the beam diameter remains less than about 75 micrometers while in the channels.

According to various embodiments, the focused line of the laser is altered with a beam expander in order to more effectively irradiate a large number of channels. For example, the laser beam can be expanded perpendicular to the capillary array. Such lengthening or "fanning out" of the laser line can facilitate positioning of the beam so that all channels are adequately irradiated. The beam can optionally be altered or redirected, as with a mirror, filter, lens, or other optical element, prior to contacting the array. For example, mirrors can be used to provide a convenient means for adjusting the direction of the laser beam to become coplanar with the channel array perpendicular to the channels. The use of mirrors, filters, lenses, etc., or any combination thereof, is optional.

A location external to the channel array to which the transparent path may be optically coupled is to be broadly understood as any point, line, or plane external to the array, including a single pixel, linear array of pixels, or planar array (two-dimensional array) of pixels. For example, the location external to the capillary array can comprise a planar surface parallel or angled with respect to the channel array. The location external to the capillary array can include an optical detector, e.g., capable of detecting fluorescence emission from a target species in a sample in a channel. In an embodiment, the optical detector is a two-dimensional image array detector. For example, the optical detector can be a charge-coupled device (CCD) or a charge-injection device (CID).

Figure 1:
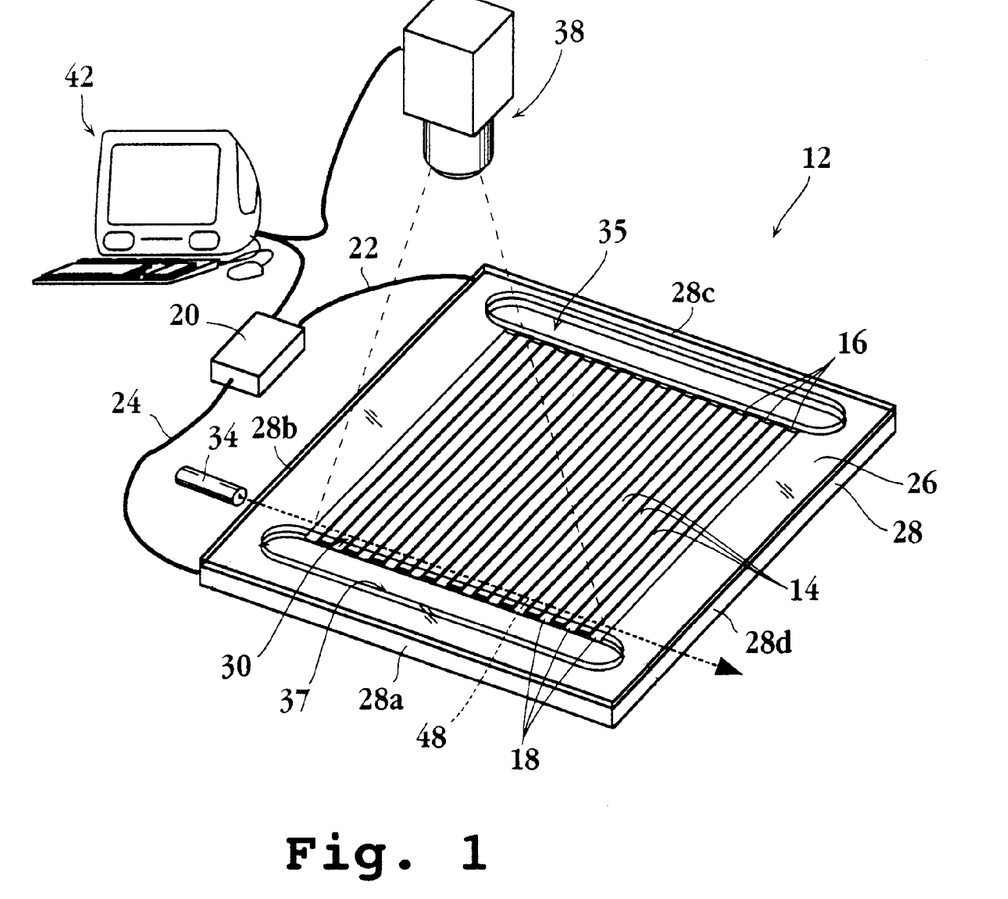
FIG. 1 is a perspective view from above of an electrophoresis system, showing a multi-channel analyte-separation device including a plurality of separation channels, a detection zone, an excitation beam source, an optical detection system, and a programmed computer control/analysis system, according to various embodiments.

Referring now to the drawings, FIG. 1 is a perspective view of an embodiment of an electrophoresis device, indicated generally by the reference numeral 12. Device 12 includes a plurality of separation channels, such as elongate channels 14, with each channel having an inlet end and an outlet end, as indicated at 16 and 18 respectively. A first lead wire 22 connects a power source 20 with a first electrode (not visible in FIG. 1) disposed in electrical communication with the inlet ends of the separation channels; and a second lead wire 24 connects source 20 with a second electrode (not visible in FIG. 1) disposed in electrical communication with the outlet ends of the separation channels. In operation, a voltage is applied between the first and second electrodes, and thereby along the channels, such that a sample zone is transported from the inlet ends, to the outlet ends of the channels, and through an on-channel detection zone, denoted as 30, located between the inlet and outlet ends.

In the arrangement of FIG. 1, device 12 is comprised of upper and lower plates, 26 and 28 respectively, with abutted confronting faces. As shown, lower plate includes end portions, 28a and 28c, and lateral side portions, 28b and 28d. Lower plate 28 is provided with a plurality of non-intersecting elongate grooves, each of roughly semi-circular or semi-oval cross-section, positioned at regular intervals (e.g., at a pitch of about 250 um) and extending along its upper face (e.g., for a length of about 5 cm); which grooves in part define separation channels 14. The lower face of plate 26 is substantially planar, and, when disposed against plate 28 as shown, further defines channels 14. Particularly, in the illustrated arrangement, the grooves of plate 28 define lower (floor) and sidewalls, or boundaries, of each channel 14 and the lower surface of plate 26 provides an upper wall for each channel 14.

Alternatively, both the upper and lower plates can be provided with complimentary sets of grooves that can be aligned with one another so that corresponding upper and lower grooves cooperate to define a plurality of elongate channels.

Instead of providing grooves in a lower plate which are covered by a planar lower surface of an upper plate, such as shown in FIG. 1, the device of the invention can include an upper plate with grooves formed along its lower surface, which can be placed over a planar upper surface of a lower plate (that is, essentially, the reverse of what is shown in FIG. 1). Moreover, although the device of the invention is illustrated as operating with the major planar surfaces of the plates disposed in a substantially horizontal fashion, the device instead could instead be configured to operate with the plates disposed substantially vertically, or tilted at a desired angle.

While the channels depicted in FIG. 1 are parallel to one another, it should be appreciated that other configurations are possible. In one embodiment, the channels converge toward one end of the device (e.g., the distance separating adjacent channels (i.e., the pitch) becomes smaller along a direction towards the outlet ends). Additionally, it should be noted that the central longitudinal axes of the channels can be straight (as shown), curved, or a combination thereof. In the embodiment of FIG. 1, the flow cross-sectional area (i.e., the cross section taken perpendicular to the direction of sample migration) is substantially the same among the various channels. In particular, the channels of FIG. 1 are all of a uniform depth (measured from the lower face of the upper plate bounding the top region of the channel to the lowermost point, or floor, of the channel groove). Such uniformity can be achieved as the ordinary result of common microfabrication methods employed in constructing the device, such as etching. However, the invention additionally contemplates channels of varying depth; which can be made, for example, by use of a two stage etching process with multiple masks.

In practice, a separation medium is injected (e.g., pressure-filled or vacuum aspirated) or otherwise provided in the separation channels of the invention to effect the electrophoretic separation of the components of the sample (s). It should be noted that the present invention contemplates the use of any suitable injection techniques; e.g., without limitation, electrokinetic injections, hydrodynamic injections, cross tee injectors and double tee injectors, etc., as known and described in the art. In one preferred embodiment, the separation medium is a flowable, non-crosslinked polymer solution.

An excitation-beam source, such as 34, is provided for stimulating emission from sample zones located in detection zone 30. In an embodiment, the light source is a laser, e.g., an argon ion laser, a solid-state laser, or the like; however, any suitable beam source can be used. As described in more detail below, in an embodiment of the present invention, an excitation-beam pathway or path extends through detection zone 30, along which an energy beam 48 generated by the beam source can pass. Such pathway is located between the inlet and outlet ends and extends along a plane defined by the channels (i.e., the pathway is co-planar with the plane of the channels). In an embodiment, the beam pathway is perpendicular to the direction of sample migration across the detection chamber, but this is not critical to the invention (i.e., the pathway can approach at an angle with respect to the direction of sample migration). What is important in this embodiment is that a beam passing along the pathway is capable of simultaneously exciting plural sample zones in respective (different) channels.

In various embodiments, such as shown in the arrangement of FIG. 1, the beam enters a lateral side 28b of lower plate 28, passes through plate 28 (including each of channels 14), and exits at an opposite lateral side 28d of plate 28. In other embodiments, a laser dump or sink can be incorporated in the plate, e.g., proximate a region of side 28d, whereat the beam can terminate after passing through the channels.

As previously mentioned, a first electrode (not visible in FIG. 1) is in electrical communication with inlet ends 16 of separation channels 14. During operation of device 12, the first electrode is maintained at a first voltage $V_1$ using power source 20. Electrical communication between the first electrode and the inlet ends of the separation channels can be established, for example, by providing an electrically conductive solution in a reservoir/loading region 35 of device 14 so that both the inlet ends of the channels and the first electrode are in contact with the conductive solution.

With continued reference to FIG. 1, each of outlet ends 18 communicates a respective channel 14 with a second reservoir 37, which reservoir is located proximate the outlet ends.

The second electrode (not visible in FIG. 1) is in electrical communication with outlet ends 18 of separation channels 14. During operation of device 12, the second electrode is maintained at a second voltage $V_2$, also using power supply 20. Preferably, electrical communication between the second electrode and second reservoir 37 is established by providing an electrically conductive solution in second reservoir 37 such that the second electrode and outlet ends 18 are in contact with the conductive solution.

The electrodes used in the device may be formed from any electrically conducting materials. Preferably, the electrodes are made from a chemically inert material, e.g., platinum, gold, stainless steel, or other relatively inert conductive material. In accordance with one embodiment of the present invention, platinum electrodes are fabricated on the top or bottom plate by RF sputtering and photolithography before the top plate is bonded to the etched bottom plate.

The electrically conductive solution used to establish electrical continuity throughout the system can be any fluid capable of transporting an electrical current. For example, the conductive solution can be an ionic solution, e.g., an aqueous solution containing a dissolved salt. In various embodiments, the conductive solution includes a buffer for stabilizing the pH of the solution. According to certain embodiments, the ionic composition of the conductive solution is the same in the separation channels, each of the electrode reservoirs, and the detection chamber.

To facilitate optical detection of sample zones in the detection zone 30, part or all of upper plate 26 covering detection zone 30 can be formed from a material which efficiently transmits light (i.e., an optically clear material), e.g., glass, quartz, clear plastic, and the like. In addition, to facilitate the introduction of an excitation light beam 48 into the detection zone to excite fluorescence of sample zones therein, part or all of the plate 28 along a region between the beam source 34 and the endmost channel 14 closest thereto can be formed from a material which efficiently transmits light. In various embodiments, the light-transmitting material does not significantly scatter light and has little intrinsic fluorescence.

Further in the embodiment of FIG. 1, a detector 38 is provided for detecting sample zones passing through the detection zone 30. The detector can be any type of detector for detecting emission of any type radiation, e.g., radioactivity, fluorescence, phosphorescence, chemiluminescence, and the like. In an embodiment, detector 38 is capable of detecting fluorescence from a plurality of locations independently and simultaneously, e.g., a CCD camera, an array of photomultiplier tubes, a diode array, and the like. As illustrated in FIG. 1, detector 38 can be connected to a computer 42 to store, analyze, and display data collected by the detector and/or to control the operation of the detector and other aspects of the device, as desired. For example, computer 42 can be programmed to control power source 20 and/or beam source 34.

It should be appreciated that, in regions of the device where it is not required or desired that radiative emission should be able to pass through, non-optically clear materials may be used, e.g., polymeric materials such as Teflon, silicone, and the like. Of course, the detection zone, as previously mentioned, preferably permits light to pass from each channel to the next channel, and to the detector.

The electrophoresis apparatus of the present invention can also include one or more additional elements typically used to conduct a capillary electrophoresis process, e.g., a temperature control device for controlling the temperature of the separation channels. Details of these and other common features of an operable capillary electrophoresis device can be found in any number of available publications, e.g., Capillary Electrophoresis Theory and Practice, Grossman and Colburn, eds., Academic Press (1992).

Various embodiments provide for reduced crosstalk, while facilitating excitation and detection. Certain embodiments, for example, utilize bandpass filters that transmit light only within a defined spectral band. For example, an excitation filter can be employed (e.g., coated upon or fixed to regions of the lower plate) that allows only light which excites a reporter of interest to strike the sample. An emission filter can be employed (e.g., coated upon or fixed to regions of the upper plate) that allows the fluorescence from the sample to pass to a detector and blocks stray light from the light source or interfering components in the sample.

Figure 2A:
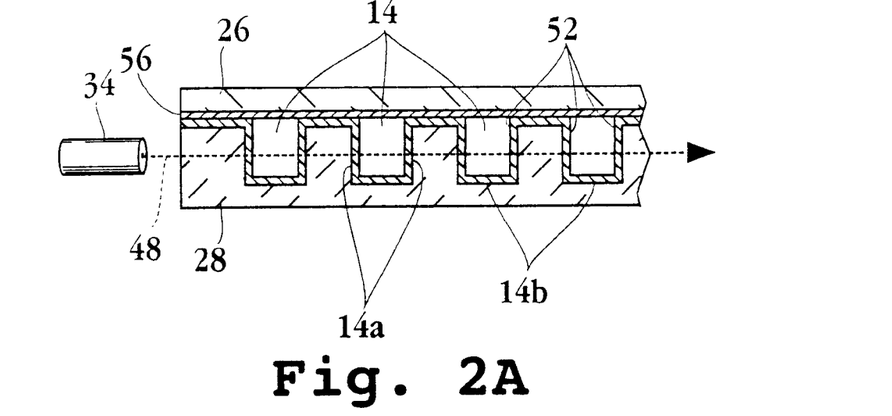
FIGS. 2A, 2B, and 2C are partial, cross-sectional views of multi-channel analyte-separation devices, according to various embodiments.
Figure 2B:
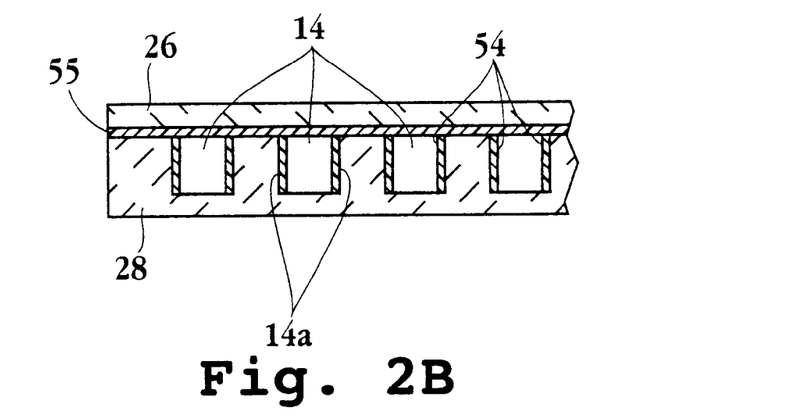
Figure 2C:
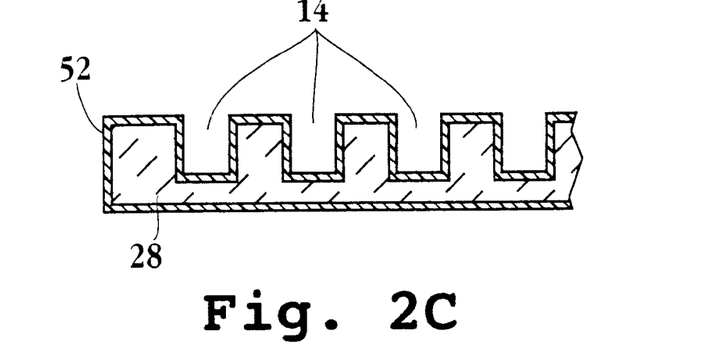
Figure 3A:
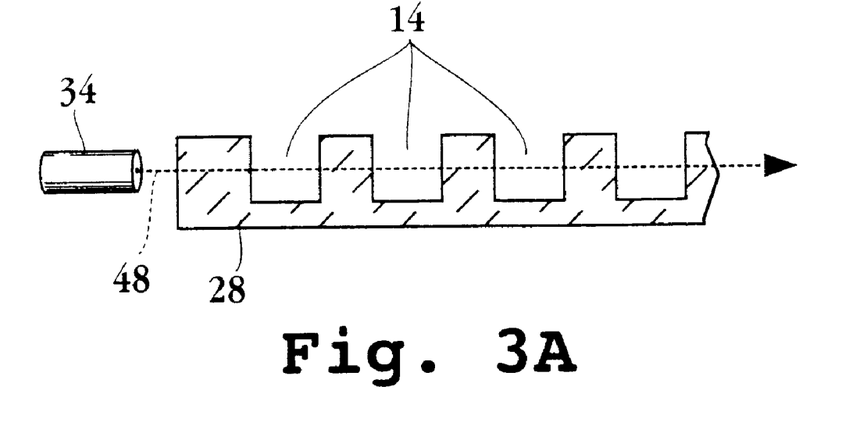
FIGS. 3A, 3B, and 3C are cross-sectional views of substrates with channels formed therein having various geometries, according to certain embodiments.
Figure 3B:
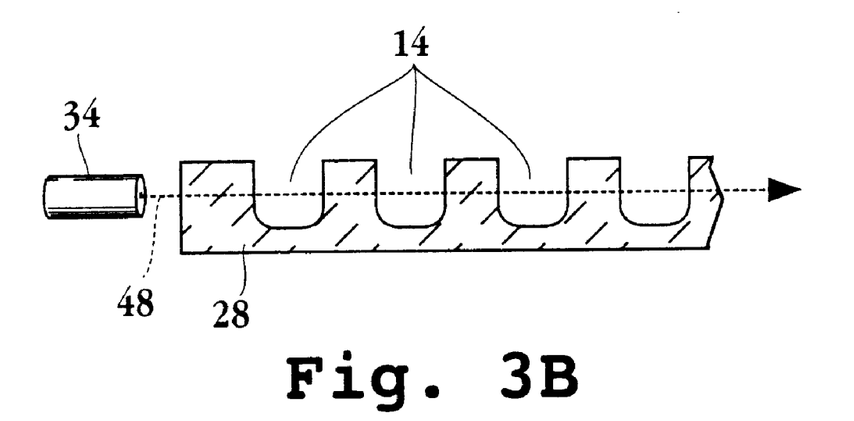
Figure 3C:
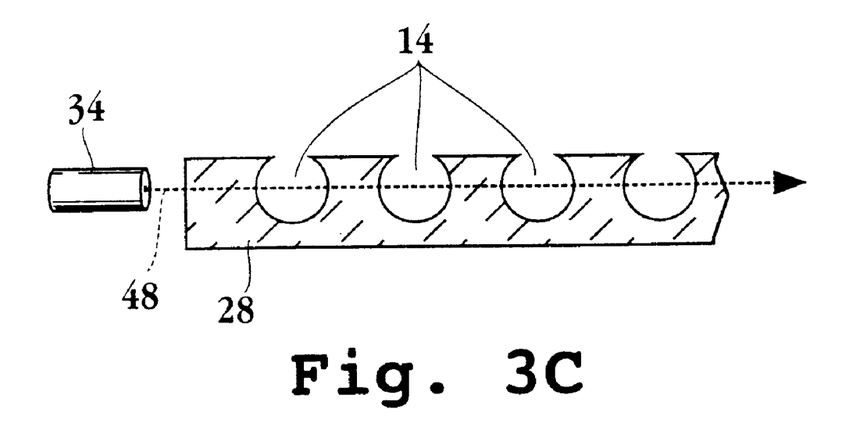

In an exemplary arrangement, as depicted in the sectional view of FIG. 2, a lower glass or plastic plate 28 is provided with spaced-apart etched channels 14. While each channel 4 is shown having vertical sidewalls 14a and a flat bottom or floor region 14b, which meet at ninety-degree angles, other channel geometries can be employed (see, e.g., FIG. 3). The sidewalls 14a of the channels have bandpass characteristics that permit passage only of the excitation (laser) beam 48 through the device (e.g., a coating material, as at 52, applied to the channel sidewalls 14a and, optionally, the floor regions 14b; or micro-optical elements 54 attached on each sidewall 14a (see FIG. 2B); or the whole lower etched plate (including the channels in their entireties) can be coated with a bandpass coating permitting only excitation light to pass (see FIG. 2C)). An upper or cover plate 26, overlaid over the channels 14, can be provided with bandpass characteristics that let only sample emission (e.g., fluorescence) to pass through (and not excitation beam wavelengths). For example, a bandpass coating material, as at 56 (FIG. 2A), can be applied to a face or face regions of the upper plate 26 that confront the lower plate 28 and channels 14, at least along regions along the detection zone. Or, a micro-optical bandpass element, such as element 55 in FIG. 2B, can be attached to the side of upper plate 26 confronting lower plate 28. By these or similar arrangements, excitation light is permitted to pass laterally through the device in a side-entry, on-channel configuration (with light of other bandwidths being substantially excluded), while fluorescent emission from sample zones is permitted to pass out of the channel to a detector (with light of other bandwidths being substantially excluded).

A number of commercial entities produce a wide range of coating technology products that can find use with the teachings herein, including bandpass filters, beamsplitters, reflectors and collectors, sputtered metals, etc. (For example: Seoul Precision Optics Co.; GM Vacuum, A Division of Navitar Coating Labs; Optical Coating Laboratory, Inc.; and Guernsey Coating Laboratories Inc.).

Optical elements and coatings useful in connection with the present teachings are described, for example, in U.S. Pat. Nos. 3,466,120; 6,112,005; 5,872,655; 4,663,557; 6,100,541; each of which is expressly incorporated herein by reference.

Figure 4:
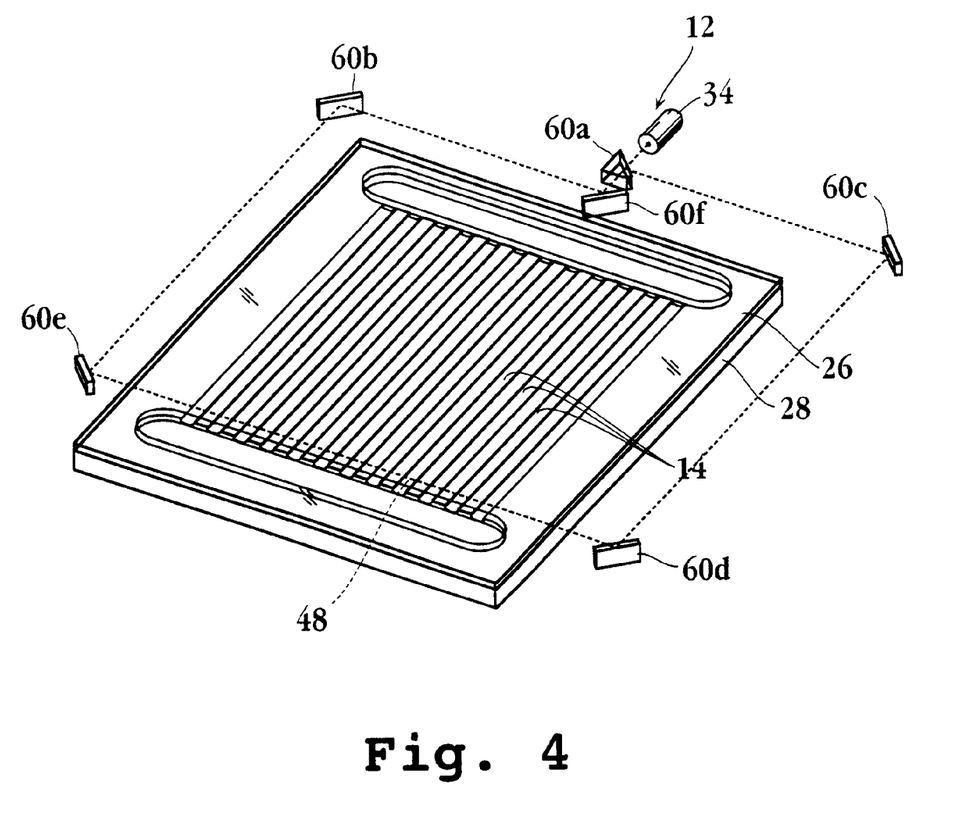
FIG. 4 is a perspective view from above of an electrophoresis system, including a multi-channel analyte-separation device including a plurality of separation channels, an excitation beam source, and optics directing an excitation beam for entry into the channel device from each lateral side thereof, according to various embodiments.

According to various embodiments, an excitation beam of light is directed toward the array from each lateral side of the device. For example, two lasers can be employed, one on each side of the device. Or, as depicted in FIG. 4, a single laser source 34 can be employed in combination with appropriate beam splitting and directing optics, such as at 60a–60f, so that light enters the array from each lateral side of the device.

It should be noted that, in some instances, one of skill in the art may choose to use less than all of the channels provided by the device of the invention to conduct separations. For instance, the left- and right-endmost channels might not be loaded with samples, while the remaining channels are so loaded; or, every other channel might be utilized, with the intervening channels remaining unused.

Various embodiments of a channel device include a substrate, with a plurality of channels formed in the substrate. Each channel includes an inlet end and an outlet end. The channels are disposed in spaced relation relative to one another, with each adjacent pair of channels being separated by a respective portion of the substrate that includes at least a region that is transparent. An excitation-beam source is adapted to direct a beam of coherent light along a beam path that intersects each of the channels at a region between the inlet and outlet ends, and further intersects the transparent region of the substrate separating adjacent pairs of channels.

According to certain embodiments, each channel includes opposed sidewalls with portions that are substantially parallel to one another. The parallel portions are at least in part transparent, and the beam path extends through the transparent, parallel portions. Such construction can be useful to avoid or reduce loss of light intensity as the beam travels through the device, from channel to channel.

All publications and patent applications referred to herein are hereby incorporated by reference to the same extent as if each individual publication or patent application was specifically and individually indicated to be incorporated by reference.

Those having ordinary skill in the art will understand that modifications are possible in the above embodiments without departing from the teachings thereof. All such modifications are encompassed within the following claims.

It is claimed:

1. A device for the analysis of one or more samples, comprising:
   a substrate;
   a plurality of adjacently arranged channels formed in said substrate, with each channel having an inlet end and an outlet end; said channels being disposed in spaced relation relative to one another, with each adjacent pair of channels being separated by a respective portion of said substrate that includes at least a region that is transparent; and
   an excitation-beam source adapted to direct an excitation beam of light along a beam path that intersects each of said channels at a region between said inlet and outlet ends and further intersects the transparent region of the substrate separating adjacent pairs of channels.

2. The device of claim 1, further comprising a cover member positioned adjacent said substrate, over said channels.

3. The device of claim 2, further comprising an emission detection system optically coupled to a region within each channel along said beam path.

4. The device of claim 1, wherein the substrate is a plate, slide, wafer or chip comprised at least in part of an optically clear material.

5. The device of claim 1, wherein the substrate is a monolithic structure.

6. The device of claim 1, wherein the substrate is a multi-laminate structure.

7. The device of claim 1, wherein each channel includes opposed sidewall regions with portions that are substantially parallel to one another.

8. The device of claim 7, wherein said transparent region comprises at least in part said parallel portions, and wherein the beam path extends through the parallel portions.

9. A device for the analysis of one or more samples, comprising:
   a substrate, including one or more transparent regions;
   a plurality of adjacently arranged, elongate separation channels formed in said substrate, with each adjacent pair of said separation channels being separated, at least in part, by at least a portion of said one or more transparent regions; and
   an excitation-beam source disposed to direct an excitation beam of light along a beam path intersecting each of said separation channels and said at least portions of said one or more transparent regions.

10. The device of claim 9, wherein said separation channels are non-intersecting.

11. The device of claim 9, wherein the substrate is a plate, slide, wafer, or chip; and wherein said separation channels are microfabricated therein.

12. A device for the analysis of one or more samples, including:
   a substrate including a plurality of adjacently arranged, non-intersecting separation channels, each channel comprising an inlet end and an outlet end;
   a wall structure separating each adjacent pair of channels, each wall structure including at least a portion that is transparent to a limited wavelength range of light;
   an excitation-beam path extending across the substrate, intersecting (i) each channel at a region between its inlet and outlet ends and (ii) each transparent portion of said wall structure.

13. The device of claim 12, further comprising:

an excitation beam source configured to direct an excitation beam of light along said excitation-beam path, said excitation beam of light being within said limited wavelength range.

14. The device of claim 13, further comprising:

an emission detection system optically coupled to a region within each channel along said excitation-beam path.

* * * * *